US008048087B2

(12) United States Patent
Rehnke (10) Patent No.: US 8,048,087 B2
(45) Date of Patent: Nov. 1, 2011

(54) APPARATUS FOR USE IN FASCIAL CLEFT SURGERY FOR OPENING AN ANATOMIC SPACE

(75) Inventor: Robert D. Rehnke, St Petersburg, FL (US)

(73) Assignee: Tyco Healthcare Group LP, Norwalk, CT (US)

( * ) Notice: Subject to any disclaimer, the term of this patent is extended or adjusted under 35 U.S.C. 154(b) by 196 days.

(21) Appl. No.: 11/974,548

(22) Filed: Oct. 15, 2007

(65) Prior Publication Data

US 2008/0045994 A1    Feb. 21, 2008

Related U.S. Application Data

(63) Continuation of application No. 10/428,252, filed on May 5, 2003, now Pat. No. 7,967,835.

(51) Int. Cl.
*A61M 29/00* (2006.01)
(52) U.S. Cl. .......................... 606/108; 600/184; 606/194
(58) Field of Classification Search .......... 606/190–195, 606/198, 108; 600/184, 201, 206, 207
See application file for complete search history.

(56) References Cited

U.S. PATENT DOCUMENTS

| | | |
|---|---|---|
| 157,343 A | 12/1874 | Molesworth |
| 1,213,005 A | 1/1917 | Pillsbury |
| 2,687,719 A | 8/1954 | Hoyt |
| 2,701,559 A | 2/1955 | Cooper |
| 2,854,983 A | 10/1958 | Baskin |

(Continued)

FOREIGN PATENT DOCUMENTS

DE    526 423    6/1931

(Continued)

OTHER PUBLICATIONS

"Endoscopically Assises 'Components Separation' for Closure of Abdominal Wall Defects", The Year Book of Plastic, Reconstructive, and Aesthetic Surgery, vol. 105, Feb. 2000, pp. 720-730, Year Book Medical Publishers, James B. Lowe, MD, Jaime R> Garza, MD, Julie L. Bowman, MD, Rod J. Rohrich, MD and W.E. Strodel, MD.

(Continued)

*Primary Examiner* — Elizabeth Houston (57) ABSTRACT

An apparatus for use in fascial cleft surgery adapted to perform blunt dissection between two layers of anatomically named fascia. The dissection performed by the apparatus extends to the limits of anatomic space defined by fusion of said two layers of fascia in a minimally invasive manner. The apparatus is formed of a hollow tube body member including a malleable introducing flange having a spoonbill-like shape. Further, the apparatus includes an elastic dissection balloon movably positioned within the applicator. The dissection balloon is reversibly expandable between a deflated condition and an expanded condition and is movable from a first storage position within the hollow tube body of the applicator to a position exterior thereof. The dissection balloon is formed of a chosen elastic material having a tensile strength less than the tensile strength of the points of fusion between two layers of fascia such that the dissection balloon fails prior to achieving pressures that would destroy the anatomic boundaries of the fascial cleft such that a working space is demonstrated not created. The apparatus also includes a gripping handle and introducing rod slideably positioned within said applicator for positioning said dissection balloon exterior said applicator to within an anatomic space for subsequent inflation and deflation. Finally, a fill tube extends through the hollow introducing rod to the dissection balloon and operably associated therewith for inflating and deflating the dissection balloon.

5 Claims, 4 Drawing Sheets

U.S. PATENT DOCUMENTS

| | | | |
|---|---|---|---|
| 2,936,760 A | 5/1960 | Gants | |
| 2,944,552 A | 7/1960 | Cannon | |
| 3,081,773 A | 3/1963 | Isaac | |
| 3,108,595 A | 10/1963 | Overment | |
| 3,259,132 A | 7/1966 | Katter | |
| 3,397,699 A | 8/1968 | Kohl | |
| 3,417,745 A | 12/1968 | Sheldon | |
| 3,459,175 A | 8/1969 | Miller | |
| 3,557,794 A | 1/1971 | Van Patten | |
| 3,626,949 A | 12/1971 | Shute | |
| 3,635,223 A | 1/1972 | Klieman | |
| 3,800,788 A | 4/1974 | White | |
| 3,841,304 A | 10/1974 | Jones | |
| 3,850,720 A | 11/1974 | Collins | |
| 3,863,639 A | 2/1975 | Kleaveland | |
| 3,882,852 A | 5/1975 | Sinnreich | |
| 3,915,171 A | 10/1975 | Shermeta | |
| 3,970,089 A | 7/1976 | Saice | |
| RE29,207 E | 5/1977 | Bolduc et al. | |
| 4,022,216 A | 5/1977 | Stevens | |
| 4,083,369 A | 4/1978 | Sinnreich | |
| 4,198,981 A | 4/1980 | Sinnreich | |
| 4,217,889 A | 8/1980 | Radovan et al. | |
| 4,271,839 A | 6/1981 | Fogarty et al. | |
| 4,276,874 A | 7/1981 | Wolvek et al. | |
| 4,295,464 A | 10/1981 | Shihata | |
| 4,299,227 A | 11/1981 | Lincoff | |
| 4,312,353 A | 1/1982 | Shahbabian | |
| 4,469,100 A | 9/1984 | Hardwick | |
| 4,479,497 A | 10/1984 | Fogarty et al. | |
| 4,484,579 A | 11/1984 | Meno et al. | |
| 4,490,137 A | 12/1984 | Moukheibir | |
| 4,493,711 A | 1/1985 | Chin et al. | |
| 4,496,345 A | 1/1985 | Hasson | |
| 4,535,757 A | 8/1985 | Webster, Jr. | |
| 4,540,404 A | 9/1985 | Wolvek | |
| 4,555,242 A | 11/1985 | Saudagar | |
| 4,572,186 A | 2/1986 | Gould et al. | |
| 4,574,806 A | 3/1986 | McCarthy | |
| 4,575,371 A | 3/1986 | Nordqvist et al. | |
| 4,585,000 A | 4/1986 | Hershenson | |
| 4,593,682 A | 6/1986 | Heckele | |
| 4,596,554 A | 6/1986 | Dastgeer | |
| 4,597,389 A | 7/1986 | Ibrahim et al. | |
| 4,610,662 A | 9/1986 | Weikl et al. | |
| 4,630,609 A | 12/1986 | Chin | |
| 4,644,936 A | 2/1987 | Schiff | |
| 4,651,717 A | 3/1987 | Jakubczak | |
| 4,685,447 A | 8/1987 | Iversen et al. | |
| 4,702,252 A | 10/1987 | Brooks et al. | |
| 4,706,670 A | 11/1987 | Andersen et al. | |
| 4,738,666 A | 4/1988 | Fuqua | |
| 4,779,611 A | 10/1988 | Grooters et al. | |
| 4,781,681 A | 11/1988 | Sharrow et al. | |
| 4,784,133 A | 11/1988 | Mackin | |
| 4,793,346 A | 12/1988 | Mindich | |
| 4,793,348 A | 12/1988 | Palmaz | |
| 4,793,359 A | 12/1988 | Sharrow | |
| 4,796,629 A | 1/1989 | Grayzel | |
| 4,798,205 A | 1/1989 | Bonomo et al. | |
| 4,800,901 A | 1/1989 | Rosenberg | |
| 4,802,479 A | 2/1989 | Haber et al. | |
| 4,832,691 A | 5/1989 | Witzel | |
| 4,862,874 A | 9/1989 | Kellner | |
| 4,921,478 A | 5/1990 | Solano et al. | |
| 4,927,412 A | 5/1990 | Menasche | |
| 4,932,956 A | 6/1990 | Reddy et al. | |
| 4,932,959 A | 6/1990 | Horzewski et al. | |
| 4,954,126 A | 9/1990 | Wallsten | |
| 4,955,895 A | 9/1990 | Sugiyama et al. | |
| 4,966,583 A | 10/1990 | Debbas | |
| 4,998,539 A | 3/1991 | Delsanti | |
| 5,030,227 A | 7/1991 | Rosenbluth et al. | |
| 5,032,113 A | 7/1991 | Burns | |
| 5,041,093 A | 8/1991 | Chu | |
| 5,041,125 A | 8/1991 | Montano, Jr. | |
| 5,042,976 A | 8/1991 | Ishitsu et al. | |
| 5,074,871 A | 12/1991 | Groshong | |
| 5,116,318 A | 5/1992 | Hillstead | |
| 5,141,494 A | 8/1992 | Danforth et al. | |
| 5,147,302 A | 9/1992 | Euteneuer et al. | |
| 5,163,949 A | 11/1992 | Bonutti | |
| 5,176,692 A | 1/1993 | Wilk et al. | |
| 5,183,463 A | 2/1993 | Debbas | |
| 5,188,596 A | 2/1993 | Condon et al. | |
| 5,188,630 A | 2/1993 | Christoudias | |
| 5,195,506 A | 3/1993 | Hulfish | |
| 5,195,507 A | 3/1993 | Bilweis | |
| 5,195,970 A | 3/1993 | Gahara | |
| 5,197,971 A | 3/1993 | Bonutti | |
| 5,201,754 A | 4/1993 | Crittende et al. | |
| 5,203,767 A * | 4/1993 | Cloyd | 604/11 |
| 5,209,725 A | 5/1993 | Roth | |
| 5,222,970 A | 6/1993 | Reeves | |
| 5,226,880 A | 7/1993 | Martin | |
| 5,232,446 A | 8/1993 | Arney | |
| 5,250,070 A | 10/1993 | Parodi | |
| 5,254,091 A | 10/1993 | Aliahmad et al. | |
| 5,258,026 A | 11/1993 | Johnson et al. | |
| 5,269,753 A | 12/1993 | Wilk | |
| 5,284,474 A | 2/1994 | Adair | |
| 5,295,994 A | 3/1994 | Bonutti | |
| 5,300,106 A | 4/1994 | Dahl et al. | |
| 5,307,814 A | 5/1994 | Kressel et al. | |
| 5,308,327 A | 5/1994 | Heaven et al. | |
| 5,309,896 A | 5/1994 | Moll et al. | |
| 5,314,443 A | 5/1994 | Rudnick | |
| 5,320,611 A | 6/1994 | Bonutti et al. | |
| 5,331,975 A | 7/1994 | Bonutti | |
| 5,334,146 A | 8/1994 | Ozasa | |
| 5,342,307 A | 8/1994 | Euteneuer et al. | |
| 5,345,927 A | 9/1994 | Bonutti | |
| 5,346,504 A | 9/1994 | Ortiz et al. | |
| 5,352,219 A | 10/1994 | Reddy | |
| 5,359,995 A | 11/1994 | Sewell, Jr. | |
| 5,361,752 A | 11/1994 | Moll et al. | |
| 5,366,478 A | 11/1994 | Brinkerhoff et al. | |
| 5,370,134 A | 12/1994 | Chin et al. | |
| 5,373,840 A | 12/1994 | Knighton | |
| 5,383,889 A | 1/1995 | Warner et al. | |
| 5,391,178 A | 2/1995 | Yapor | |
| 5,400,773 A | 3/1995 | Zhu et al. | |
| 5,402,772 A | 4/1995 | Moll et al. | |
| 5,425,357 A | 6/1995 | Moll et al. | |
| 5,431,173 A | 7/1995 | Chin et al. | |
| 5,439,476 A | 8/1995 | Frantzides | |
| 5,445,990 A | 8/1995 | Yook et al. | |
| 5,450,843 A | 9/1995 | Moll et al. | |
| 5,452,732 A | 9/1995 | Bircoll | |
| 5,454,365 A | 10/1995 | Bonutti | |
| 5,458,639 A | 10/1995 | Tsukashima et al. | |
| 5,468,248 A | 11/1995 | Chin et al. | |
| 5,480,379 A | 1/1996 | La Rosa | |
| 5,496,276 A | 3/1996 | Wang et al. | |
| 5,496,345 A | 3/1996 | Kieturakis et al. | |
| 5,514,091 A | 5/1996 | Yoon | |
| 5,514,153 A | 5/1996 | Bonutti | |
| 5,522,788 A | 6/1996 | Kuzmak | |
| 5,540,711 A | 7/1996 | Kieturakis et al. | |
| 5,588,951 A | 12/1996 | Zhu et al. | |
| 5,591,183 A | 1/1997 | Chin | |
| 5,593,418 A | 1/1997 | Mollenauer | |
| 5,601,581 A | 2/1997 | Fogarty et al. | |
| 5,601,589 A | 2/1997 | Fogarty et al. | |
| 5,607,443 A | 3/1997 | Kieturakis et al. | |
| 5,632,761 A | 5/1997 | Smith et al. | |
| 5,634,935 A | 6/1997 | Taheri | |
| 5,653,726 A | 8/1997 | Kieturakis | |
| 5,667,480 A | 9/1997 | Knight et al. | |
| 5,690,668 A | 11/1997 | Fogarty et al. | |
| 5,695,514 A | 12/1997 | Chin | |
| 5,702,416 A | 12/1997 | Kieturakis et al. | |
| 5,707,382 A | 1/1998 | Sierocuk et al. | |
| 5,722,934 A | 3/1998 | Knight et al. | |
| 5,730,748 A | 3/1998 | Fogarty et al. | |
| 5,730,756 A | 3/1998 | Kieturakis et al. | |
| 5,762,604 A | 6/1998 | Kieturakis | |

| | | | |
|---|---|---|---|
| 5,772,680 A | 6/1998 | Kieturakis et al. | |
| 5,800,394 A * | 9/1998 | Yoon et al. | 604/101.05 |
| 5,814,059 A | 9/1998 | Hart et al. | |
| 5,814,060 A | 9/1998 | Fogarty et al. | |
| 5,836,961 A | 11/1998 | Kieturakis et al. | |
| 5,843,116 A | 12/1998 | Crocker et al. | |
| RE36,043 E | 1/1999 | Knighton | |
| 5,860,997 A | 1/1999 | Bonutti | |
| 5,868,775 A | 2/1999 | Bircoll | |
| 5,871,497 A | 2/1999 | Young | |
| 5,873,889 A | 2/1999 | Chin | |
| 5,902,316 A | 5/1999 | Mollenauer | |
| 5,968,066 A | 10/1999 | Fogarty et al. | |
| 6,013,090 A | 1/2000 | Fogarty et al. | |
| 6,015,421 A | 1/2000 | Echeverry et al. | |
| 6,055,989 A | 5/2000 | Rehnke | |
| 6,102,928 A | 8/2000 | Bonutti | |
| 6,142,936 A | 11/2000 | Beane et al. | |
| 6,193,653 B1 | 2/2001 | Evans et al. | |
| 6,277,137 B1 | 8/2001 | Chin | |
| 6,312,442 B1 | 11/2001 | Kieturakis et al. | |
| 6,368,337 B1 | 4/2002 | Kieturakis et al. | |
| 6,595,010 B2 | 7/2003 | Sauterleute et al. | |
| 6,764,497 B2 | 7/2004 | Fogarty et al. | |
| 6,979,318 B1 * | 12/2005 | McDonald et al. | 604/158 |
| 6,989,018 B2 | 1/2006 | Fogarty et al. | |
| 7,037,317 B2 | 5/2006 | Hermann et al. | |

FOREIGN PATENT DOCUMENTS

| | | |
|---|---|---|
| EP | 0 492 361 | 7/1992 |
| EP | 0 630 659 | 12/1994 |
| WO | WO 82/00408 | 2/1982 |
| WO | WO 93/24172 | 12/1993 |

OTHER PUBLICATIONS

"Components Separation: A Method for Closure of Abdominal Wall Defects", The Year Book of Plastic, Reconstructive, and Aesthetic Surgery, vol. 86, Sep. 1990, pp. 519-526, Year Book Medical Publishers, O.M. Ramirez, E.J. Ruas and A.L. Dellon.

"The Oncologic Risk of Skin Preservation at Mastectomy When Combined With Intermediate Reconstruction of The Breast", Surgery, Gynecology and Obstetrics, vol. 172, Jan. 1991, pp. 17-20, Publisher: Franklin H. Martin Memorial Foundation, etc., Stephen.S. Kroll, MD, Frederick Ames, MD, S. Eva Singletary, MD, and Mark A.. Schusterman, MC.

G. Hauer, et al. "Endoscopic Subfascial Discission of Perforating Veins" *Surgical Endoscopy*, 2(1):5-12 (1988).

W.R. Dimitrie et al., "A Quick and Atraumatic Method of Autologous Vein Harvesting Using the Subcutaneous Extraluminal Dissector" *J. Cardiovasc Surg*, 28:103-111 (1987).

W. Meldrum-Hanna et al., "Long Saphenous Vein Harvesting" *Aust. N.Z.J. Surg*, 56:923-924 (1986).

Lam et al., "Surgical Procedure for Uncomplicated (Routine) Female Stress Incontinence", *Urologic Clinics of North America*, 18(2) (1991).

* cited by examiner

APPARATUS FOR USE IN FASCIAL CLEFT SURGERY FOR OPENING AN ANATOMIC SPACE

CROSS-REFERENCE TO RELATED APPLICATIONS

This application is a continuation of U.S. patent application Ser. No. 10/428,252, filed May 5, 2003 now U.S. Pat. No. 7,967,835, the disclosure of which is hereby incorporated by reference in its entirety.

BACKGROUND OF THE INVENTION

1. Field of the Invention

The present invention pertains generally to the field of surgical apparatus for opening an anatomic space. More particularly, the present invention pertains to surgical apparatus for use in fascial cleft surgery for tissue dissection wherein a balloon device performs the function of tissue dissection in a minimally invasive manner.

2. Description of the Prior Art

The American Cancer Society estimates that in 2001, 190,000 women were diagnosed with breast cancer. Approximately one in eight women in the U.S. will develop breast cancer in their lifetime. This makes breast cancer the most common cancer among women. These statistics have made breast cancer one of the most pressing issues in women's healthcare today.

The American Society of Plastic Surgeons reports a 174% increase in breast reconstruction procedures between 1992 and 2001, with 81,089 women having reconstructive procedures last year. This trend should increase exponentially as the baby boomer generation matriculates into the high risk age group. In 1998 the Woman's Health and Cancer Rights Act (WHCRA) was passed. This federal law mandates insurance coverage for breast reconstruction following mastectomy. These demographics should make surgical treatment of breast cancer one of the most pressing issues for insurers over the next decade.

The mainstay of breast cancer therapy is surgery. Treatment falls into two categories: 1) breast conservation therapy—consisting of a lumpectomy and axillary node dissection followed by radiation; and 2) Modified radical mastectomy.

Of the roughly 190,000 new cases of breast cancer each year, approximately 100,000 will undergo modified radical mastectomy. Breast reconstruction has long been an option for women who undergo mastectomy. Over the last twenty years this has evolved from a three stage procedure to a one step operation performed at the same time as the mastectomy. Immediate reconstruction at the same time as a skin sparing mastectomy has been referred to as minimally invasive treatment of breast cancer.

Skin Sparing Mastectomy with Immediate Breast Reconstruction

Standard surgical treatments for breast cancer destroy the important connections of the skin of the breast to the chest wall. In addition it leaves a long scar, which covers the entire chest. This creates unnecessary damage that is difficult to reconstruct. Minimally Invasive surgical treatment of breast cancer begins with a skin-sparing mastectomy performed through a circular incision made just outside of the areolar border. In the skin-sparing mastectomy, the skin covering the breast is lifted off the breast tissue, which is removed along with the nipple, areola, and the lymph nodes. The oncologic safety efficacy of skin-sparing mastectomy had been established in the literature with reports such as that by Schusterman out of M. D. Anderson in a report in 1991 from SG&O [The Oncologic Risk of Skin Preservation at Mastectomy When Combined With Immediate Reconstruction of the Breast, Kroll, S. S., Schusterman, M. A. & others. Surgery, Gyn. And Obstetrics, January 1991 Vol. 172, pgs 17-20.]. In this paper the authors described 100 cases of immediate breast reconstruction following skin-sparing mastectomies. In their series, the percentage of local recurrence was 1.2%, which is better than most standard modified radical mastectomy series.

The preservation of the skin covering the breast during mastectomy obviates the need for tissue expanders and thus allows for completion of the reconstruction at the same time as mastectomy. Preservation of the attachment of the breast skin to the chest wall is an important principle of the skin-sparing technique. This is important especially at the inferior and lateral aspect of the breast. It is these attachments of the skin to the chest wall, which give the breast its aesthetic form. Additionally, blood supply through lateral perforators at the lateral aspect of the breast can also be preserved thus insuring the viability of the skin flaps. Removing all of the breast tissue, without going beyond the anatomic boundaries of the breast (and thus destroying the attachment of the skin overlying the breast to the chest wall) becomes the critical factor in this procedure. Understanding of the nature of fascial clefts and their application to breast anatomy is greatly helpful in skin sparing mastectomy.

The breast gland is contained between two layers of superficial fascia. The sub glandular space is in fact a fascial cleft between the superficial fascia on the deep surface of the breast and the deep fascia of the pectoralis major muscle and chest wall. This cleft has anatomic boundaries where all of these layers of fascia fuse and define the limits of the breast. These fusion points have been referred to as the "circum-mammary ligament". The application of fascial cleft surgery to skin sparing mastectomy performs this critical dissection in a quick, easy and accurate manner. What has yet to be developed, that the present invention provides for, is an instrument specifically designed for performance of fascial cleft surgery in skin sparing mastectomies.

Once the breast specimen has been removed an empty envelope of breast skin remains and requires filling. This can be done in certain patients with autologous tissue in the form of a TRAM (tummy tuck) flap. However, most patients are either poor candidate for this invasive reconstructive surgery or do not desire the lengthy recovery that is associated with it. The majority of patients will opt to fill the void created by the mastectomy with breast implants. Prior to the placement of these implants a muscle flap from the underlying pectoralis major muscle and the latissimus dorsi muscle (from the back), is mobilized to cover the opening created by the mastectomy. The implant is placed under the muscle, which gives a natural softness to the breast and the skin repositioned over it. Following this a full thickness skin graft from the groin is placed on the top of the latissimus flap to reconstruct the areola. The back muscle is removed through an incision which runs horizontally and can be easily hidden by a bra or bathing suite. All this can be performed at the same operation as the mastectomy.

Because the skin overlying the breast and its attachments to the chest wall has been preserved, placement of a breast implant is a relatively straight forward procedure. For this reason it can be performed safely and effectively at the same time as the mastectomy. These procedures are not terribly invasive and do not create a difficult recovery. For this reason patients who are healthy without serious medical conditions can easily have this performed on an outpatient basis (23 hour stay). The use of minimally invasive approaches to mastectomy and immediate reconstruction reduces the number of surgeries required to one. This yields benefits to the patient and their families as well as providers who are responsible for the cost of reconstruction.

The concept of minimally invasive surgery therefore does not require the use of one of the most important tool of the surgical movement—the endoscope. It does however require a surgical philosophy of first doing no unnecessary harm to surrounding anatomic tissues and structures in the process of accomplishing the surgical operational plan. An analogy can be drawn to modern military forces which use smart bombs and high tech equipment to avoid civilian casualties and minimize friendly fire injuries. This often involves the use of small incisions when compared to standard open surgery, but more importantly it minimizes unnecessary dissection that might destroy anatomic form and function leading to prolonged recovery or post operative disability or deformity. Minimally invasive ventral hernia repair illustrates this concept nicely.

Ventral incisional hernias are known to occur following 10% of all laparotomies. Each year 100,000 ventral hernias are repaired in the US (with another 100,000 estimated in the rest of the world). Primary closure has a recurrence rate as high as 50%. This has led to the wide acceptance of repair techniques using synthetic mesh implants as patches to cover abdominal wall defects. This however fails to restore functional strength of the abdominal wall and is still associated with an unacceptably high rate of recurrence (20 to 25% in most series). Mesh repairs have the additional drawback of potential devastating entero-cutaneous fistulas and infections.

The "Components Separation" technique for ventral hernia repair, introduced by plastic surgeon, Oscar Ramirez in 1990, marked a novel approach to this difficult clinical problem. The technique involves wide undermining of the abdominal skin to expose the surface of the anterior abdominal wall, after standard exposure and excision of the hernia sac. Long relaxing incisions are made through anterior fascia one centimeter lateral and parallel to the semi-lunar line. Next, open blunt dissection is performed in a fascial cleft between the layers of the external oblique and internal oblique muscles. Dissection to the borders of this fascial cleft allows for mobilization of the rectus muscles to the midline to achieve direct closure without tension. Midline closure obviates the need for mesh and restores proper function and strength of the anterior abdominal wall.

Despite dramatic reduction in recurrence rates (to single digits in multiple published reports) several factors have prevented widespread adoption of this procedure. First, the vast majority of reports on this technique have been published in the Plastic Surgery literature, while 95% of ventral hernias are performed by general surgeons. Second, the wide undermining of abdominal skin and management of resulting skin excess is outside the comfort zone of most general surgeons. In fact, ischemia of the edges of these skin flaps with resultant wound separation and infection has been the major criticism of the Ramirez technique. Finally, the components separation technique requires more effort and time, than the mesh repair, due to the need for open exposure of the anterior abdominal wall. Endoscopically assisted components separation, reported first by Lowe, Rohrich, et. al. addressed these concerns and has shown it to be a safe and effective method of repair of complicated and recurrent midline ventral hernias (Lowe J B, Garza J R, Bowman J L, Et al. Endoscopically assisted "components separation" for closure of abdominal wall defects. Plast Reconstr Surg 2000; 105:720-29).

The use of Fascial Cleft Surgery allows for quick and easy performance of endoscopically assisted components separation repairs. It alleviates the need for undermining of skin and accomplishes dissection of the abdominal wall components (external oblique and internal oblique muscles), with the new surgical instrument constituting the present invention, to the limits of the fascial cleft. Endoscopy allows for release of the external oblique fascia under direct visualization. This maneuver is performed as quickly and easily as introduction of trocars in laparoscopic procedures. The remainder of the procedure is reduced to direct closure of the midline defect. Attempts by Lowe and others to use existing balloon dissectors based on the Kieturakis prior art failed to dissect the fascial cleft to its anatomic borders due to limitations of its design and the inelastic nature of the balloon. This required multiple insertions of the balloon into the cleft between the external and internal oblique muscles. It also failed to fully dissect the entire anatomic space since dissection was limited to the dimensions of the device. Perhaps this incomplete dissection resulted in insufficient release of tension when the midline was closed and accounts for the higher recurrence of hernia formation in Lowe's endoscopic series when compared to his open components separation repairs. This makes a strong argument for a new improved surgical device for performing minimally invasive ventral hernia repair with fascial cleft dissection.

Minimally Invasive Surgery

Minimally invasive surgery was born in the "fertile crescent" of the peritoneal cavity. Complex surgical maneuvers performed through small incisions are enabled by opening the potential space that is the peritoneal cavity through gas insufflation. Gas is used to inflate the anatomic space until the anatomic boundaries are reached. Once the anatomic potential space has been opened and inflated to its limits an endoscope is inserted and the space is inspected and manipulated as necessary. Minimally invasive procedures outside the peritoneum have defied exploration because of the lack of an easily accessible and inflatable working space.

Bonutti, U.S. Pat. No. 5,163,949, recognized the need for retraction of soft tissues when working outside the peritoneal cavity. He envisioned cannulas and catheters that were inserted into a mass of tissue and used inflatable devices to expand perpendicular to the axis of the cannula. This created a working space when the distal end of the cannula expanded and caused separation along natural tissue planes for a substantial distance.

A surgical balloon dissector and method of use is disclosed in U.S. Pat. No. 5,496,345, to Kieturakis et al. This device provides for an expansible tunneling apparatus that creates an anatomic work space in a body mass. It is comprised of a tubular member with a rigid tunneling shaft having a blunt tipped obturator for tunneling through tissue to a desired location for dissection. The device contains a non-elastomeric balloon designed in the shape of a mantaray. This balloon on the distal end of the shaft is positioned in the preferred embodiment behind the inguinal region in the preperitoneal space after being introduced through an incision at the umbilicus.

In Johnson et al., U.S. Pat. No. 5,258,026, Johnson embellished Bonutti's work by describing a method for dissection using a tissue expander. He described use of a hollow endotube with a bullet shaped obturator that is used to tunnel to a desired location between skin and subcutaneous fat, skin and bone, skin and muscle or skin and fascia. The endotube is then used to deliver a tissue expander to the location which is then expanded to create spaces, cavities, or pockets in the body. He recommends overfilling the inflatable hollow member by 50%. The preferred embodiment of this method is a breast augmentation performed through an umbilical incision.

Johnson is still limited to creating spaces based on the dimensions of the device, even when the device was "overfilled by 50%". Johnson was also imprecise in the tunneling of the endotube and positioning of the inflatable dissector. Its method lacked a sophisticated understanding of soft tissue anatomy and implied that it is practical and possible to create a dissection space at any desired location or plane of tissue. This is in fact not the case. For instance, it is not possible to perform minimally invasive blunt dissection with an inflatable device within the subcutaneous fat as Johnson claims. This is because of the existence of anatomic entities named "vertical cutaneous ligaments" which run up vertically from superficial fascia (which is in the horizontal plane) to the skin. This anatomic construct is analogous to a honey comb filled with honey, where the fat is the honey and the comb is the fascia and ligaments. Dissection in this natural plane (i.e. the subcutaneous plane) can only be performed with sharp dissection, or a constant combination of sharp and blunt dissection as in face lift surgery. This is because the vertical cutaneous ligaments cross the horizontal subcutaneous plane and resist blunt dissection.

In Rehnke, U.S. Pat. No. 6,055,989, fascial cleft surgery was first disclosed. A fascial cleft is an anatomic potential space between layers of fascia throughout the body with defined limits or boundaries, much like the peritoneal cavity. Fascial cleft surgery enables minimally invasive endoscopic surgery outside the peritoneal cavity in all regions of the body. Fascial cleft surgery not only respects the soft tissue anatomic layers and boundaries but takes full advantage of their existence. Unlike the peritoneal cavity, in laparoscopy, the potential space between layers of fascia has more cohesion and can not be separated into a true working space by CO2 gas insufflation. A specialized dissection instrument is required. The present invention relates to a specialized surgical instrument for use in fascial cleft surgery.

The patent to Bonutti, U.S. Pat. No. 5,163,949, discloses the use of cannulas to tunnel through a body mass indiscriminately and CREATES a work space in unspecified natural planes. The surgical apparatus comprising the present invention for use in fascial cleft surgery for tissue dissection utilizes a balloon device to perform the function of tissue dissection in a minimally invasive manner. The inflatable device of the Bonutti apparatus determines the size of the work space and retracts tissue based on the construct of the device shape. This method does nothing to delineate the size or boundaries of an underlying anatomic space. Bonutti's method relies on the design of the instrument rather than the inherent anatomic design of the body to create a space.

The surgical apparatus comprising the present invention uses open dissection, through a small incision, to a specific anatomic cleft between layers of known named fascia to enter a particular fascial cleft, which is analogous to the peritoneal cavity in laparoscopy. The inflatable device comprising the present invention, which has no predetermined inflated fixed shape or dimensions, is delivered into the fascial cleft without any tunneling through layers of tissue. The inflatable balloon apparatus of the present invention is designed to fail before achieving pressures that would destroy the anatomic boundaries of the fascial cleft. The pressure generated by the expansion of the device is weaker than the integrity of the fascia and the points of fusion between the two layers of fascia. The working space is not created, it is demonstrated. This is a fundamental difference in philosophy of dissection which requires a distinct difference in design and use of the instrument.

U.S. Pat. No. 5,496,345, to Kieturakis et al. discloses a device used for practicing a method of dissection. The only anatomic distinction made is in regard to the preperitoneal space in the preferred embodiment of inguinal hernia repair. It also creates a work space of dimensions that follow the design of the device rather than demonstrate existing anatomic spaces. The patent teaches a "balloon is formed of a non-elastomeric material; it is a volume-limited balloon to prevent overexpansion." This reflects a fundamental departure from the philosophy regarding minimally invasive soft tissue dissection. The shape of the Kieturakis device has a non-elastic balloon of designed dimensions that creates a work space according to its fixed size. This is undesirable in the '989 Rehnke method of fascial cleft surgery. The present invention requires an elastic device which expands until it reaches the anatomic limits of the fascial cleft.

The Kieturakis device is made of a hollow tube with a rigid shaft with a hemispherical or ellipsoidal obturator at the end, designed to tunnel through tissue. This sort of straight rigid shaft with a bullet shaped obturator is highly undesirable if one wants to keep the device within a specific anatomic cleft during introduction of the inflatable member. The Present invention comprises a flat, beveled spoonbill distal end with a malleable end ideally suited for inserting the inflatable device of the present invention into a fascial cleft of curvilinear proportions without straying from that space. The Kieturakis device with its rigid shaft and obturator is prone to tunneling out of a desired fascial cleft.

In Johnson et al., U.S. Pat. No. 5,258,026, augmentation is disclosed wherein the surgery is performed through an umbilical incision. Johnson teaches the use of a hollow endotube with a bullet shaped nose piece for tunneling from a remote incision to a desired location for creation of a space, cavity, or pocket. This method of dissection relates to dissection of soft tissues in various regions within subcutaneous fat, between skin and bone, skin and muscle, or skin and fascia. It also describes dissection between fat and bone, fat and muscle fat and fascia and peritoneum and fascia; including between tissue and: bladder, nerves, blood vessels and muscle. This intrusive approach to invasive dissection generally disregards human anatomy. It is a method groping in anatomic darkness, hoping to hit an undefined mark. The use of a penetrating obturator for tunneling has the same design drawbacks of the Kieturakis device. The expander or prosthesis that is inflated to "overfilling . . . by about 50%", relates to breast implants and tissue expanders. Thus this method patent advocates use of relatively inelastic prostheses that are "overfilled" to create a pocket; as apposed to the present invention device which is completely elastic and follows the design of the anatomic space and is stopped by the anatomic boundaries of the fascial cleft, rather than the point 50% beyond a prescribed fill volume.

Young, U.S. Pat. No. 5,871,497, teaches a device for dissecting along natural tissue planes to create a tissue pocket to hold the device which is left in place to perform traditional tissue expansion over a long term (days and months). It uses a device with a rigid base to establish the footprint and orientation of the expansion effort. This sort of device clearly has no use in fascial cleft surgery.

Accordingly, there is a need for improved surgical apparatus for use in fascial cleft surgery for minimally invasive surgical dissection to overcome the aforementioned disadvantages in the prior art.

The use of surgical dissection tools of known designs and configurations is known in the prior art. More specifically, balloon disectors of known designs and configurations heretofore devised and utilized for the purpose of surgical dissection through known methods and apparatuses are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, the aforementioned patents do not describe a surgical apparatus for use in fascial cleft surgery for tissue dissection wherein a balloon device performs the function of tissue dissection in a minimally invasive manner.

In this respect, surgical apparatus for use in fascial cleft surgery for tissue dissection according to the present invention substantially departs from the conventional concepts and designs of the prior art, and in doing so provides an apparatus primarily developed for the purpose of utilizing a balloon device for performing the function of tissue dissection in a minimally invasive manner.

Therefore, it can be appreciated that there exists a continuing need for a new and improved surgical apparatus for use in fascial cleft surgery for tissue dissection which can be used for performing the function of tissue dissection in a minimally invasive manner. In this regard, the present invention substantially fulfills this need.

SUMMARY OF THE INVENTION

In view of the foregoing disadvantages inherent in the known types of surgical tools of known designs and configurations now present in the prior art, the present invention provides an improved surgical apparatus for use in fascial cleft surgery for tissue dissection wherein a balloon device performs the function of tissue dissection in a minimally invasive manner.

To attain this, the present invention essentially comprises a surgical apparatus with balloon dissector. The present invention is comprised of a plurality of components. Such components in their broadest context include an applicator, an elastic dissection balloon movably positioned within said applicator, and a hollow introducing rod slideably positioned within said applicator for positioning said dissection balloon exterior said applicator to within an anatomic space for subsequent inflation and deflation. Such components are individually configured and correlated with respect to each other so as to attain the desired objective.

The present disclosure provides a surgical apparatus for use in a method of performing any combination of the distinct functions of dissecting, expanding, and sizing in serial order. The apparatus preferably utilizes an elastic balloon formed of a chosen elastic material having a tensile strength less than the tensile strength of the points of fusion between two layers of fascia such that the dissection balloon fails prior to achieving pressures that would destroy the anatomic boundaries of the fascial cleft such that a working space is demonstrated not created, for example, to dissect tissue layers to open a tissue pocket or working space, to provide serial tissue expansion and if necessary to thereafter size the dissected space.

A preferred method of use of the apparatus forming the present invention is directed to all areas outside the peritoneal cavity where minimally invasive surgical dissection is performed using fascial cleft surgery. Direct open dissection is performed through a minimal incision to access the desired fascial cleft. Then the device is inserted between the two layers of fascia which define the cleft. The elastic balloon is introduced to the space and inflated until the anatomic dimensions of the cleft stop the dissection. The anatomy thus having been demonstrated it can be examined and sized, expanded, or surgically manipulated as desired.

One such application which has already been described is skin sparing mastectomy. In this case the device is used on the chest to dissect the retro mammary fascial cleft and demonstrate the extent, size, and exact location of the anatomic boundaries of the breast. These are critical steps in the performance of this minimally invasive procedure.

A second application in the abdominal wall makes use of fascial cleft surgery in performing endoscopically assisted ventral hernia repair. A technique known as components separation technique requires separation of the outer layer of the abdominal wall from the two inner layers to allow advancement of the attached rectus muscle for closure of the midline without tension. This technique repairs ventral hernias without the use of mesh on lays or inlays. Traditional open techniques require extensive undermining of skin to expose the anterior abdominal wall so that open dissection of the fascial cleft, between the lateral abdominal wall muscles, can be bluntly dissected to their anatomic boundaries at the lumbar region. This destroys the circulation of blood to the skin edges of the open wound and leads to a high incidence of wound complications. A minimally invasive approach uses a small incision over the lateral abdominal wall and performs a minimal open dissection down to the fascial cleft between the lateral abdominal wall muscles. The present invention provides for introduction of an elastic inflatable dissector into this fascial cleft which is inflated until dissection reaches the anatomic limits of the cleft. The balloon can be left in place in the expanded condition for a period of time during the procedure to perform immediate tissue expansion prior to release of the fascia, lateral to the rectus muscles, prior to advancement to the midline for closure. This illustrates the ability to perform complex soft tissue surgery without unnecessary collateral damage to the abdominal wall skin and its circulation.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved surgical apparatus for use in fascial cleft surgery for tissue dissection wherein a balloon device performs the function of tissue dissection which has all of the advantages of the prior art of known designs and configurations and none of the disadvantages.

It is another object of the present invention to provide a new and improved balloon dissection apparatus which may be easily and efficiently manufactured and marketed.

Lastly, it is an object of the present invention to provide a new and improved surgical apparatus for use in fascial cleft surgery adapted to perform blunt dissection between two layers of anatomically named fascia wherein the dissection extends to the limits of anatomic space defined by fusion of said two layers of fascia in a minimally invasive manner. The apparatus comprises an applicator formed of a hollow tube body member having an open proximal end and an open distal end. Further included is a spoonbill-like shaped malleable introducing flange formed at the distal end of the applicator. An elastic dissection balloon is movably positioned within the applicator adjacent the introducing flange. The dissection balloon is reversibly expandable between a deflated condition and an expanded condition and is movable from a first storage position within the hollow tube body of the applicator to a position exterior thereof. Also, wherein the dissection balloon is formed of a chosen elastic material having a tensile less than the tensile strength of the points of fusion between two layers of fascia such that the dissection balloon fails prior to achieving pressures that would destroy the anatomic boundaries of the fascial cleft such that a working space is demonstrated not created. A gripping handle is coupled to the applicator at the open proximal end thereof. The gripping handle includes a thumb engaging recess corresponding to the introducing flange for allowing a user to judge the orientation of the introducing flange during use of the apparatus. A hollow introducing rod is slideably positioned within the applicator. The introducing rod has a first end terminating in a concave surface positioned adjacent the dissection balloon for positioning the dissection balloon exterior the applicator to within an anatomic space for subsequent inflation and deflation. Finally, a fill tube extends through the hollow introducing rod to the dissection balloon and operably associated therewith for inflating and deflating the dissection balloon.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

With reference now to the drawings thereof, the preferred embodiment of the new and improved surgical apparatus for use in fascial cleft surgery for tissue dissection wherein a balloon device performs the function of tissue dissection in a minimally invasive manner embodying the principles and concepts of the present invention and generally designated by the reference numeral 10 will be described.

The present invention, the surgical apparatus 10, is comprised of a plurality of components. See FIG. 1. Such components in their broadest context include an applicator, an elastic dissection balloon movably positioned within said applicator and a hollow introducing rod slideably positioned within said applicator for positioning said dissection balloon exterior said applicator to within an anatomic space for subsequent inflation and deflation. Such components are individually configured and correlated with respect to each other so as to attain the desired objective.

The surgical apparatus comprising the present invention is for use in fascial cleft surgery and is adapted to perform blunt dissection between two layers of anatomically named fascia 12. The dissection extends to the limits of anatomic space defined by fusion of said two layers of fascia in a minimally invasive manner. In certain areas of the body, points of fusion between layers of fascia create well-defined boundaries which may be used to advantage by the surgeon during dissection, particularly balloon dissection, to create an anatomically well-defined space between layers joined by such ligaments 14. Ligaments which create such useful boundaries, for example, in: the chest and breast, between the layers of the abdominal wall, in the upper and lower extremities, in the back, and in the head and neck. See FIGS. 5-8.

Figure 1:
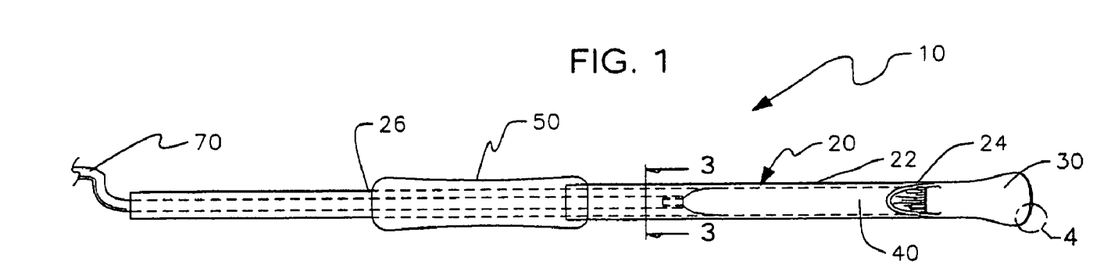
FIG. 1 is an top plan view of the surgical apparatus for use in fascial cleft surgery forming the present invention having the dissection balloon in a first storage position.

The apparatus includes an applicator 20 as shown in FIG. 1. The applicator is formed of a hollow tube body member 22 and has an open proximal end 24 and an open distal end 26. The applicator forms the main housing of the present invention.

Further, the present invention includes a malleable introducing flange 30. The introducer flange is formed at the distal end of the applicator. The introducer flange has a spoonbill-like shape. In use, the flange serves to spread tissue and position the distal end of the applicator with a space defined by a fascial cleft. As an alternate embodiment, the introducer flange is malleable for allowing user modification corresponding to individual anatomy. In one particular embodiment, the malleable introducing flange is reconfigurable from a first configuration to a second configuration upon application of force, wherein the introducing flange remains in the second configuration when the force is removed.

Figures 1A, 2:
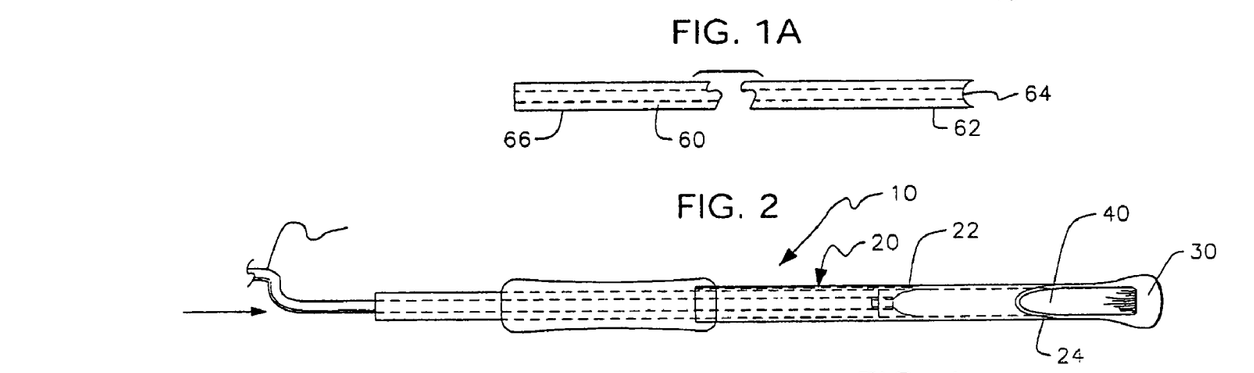
FIG. 1a is an top plan view of the introducing rod component thereof
FIG. 2 is a top plan view thereof showing the dissection balloon in a semi-deployed position.
Figure 3:
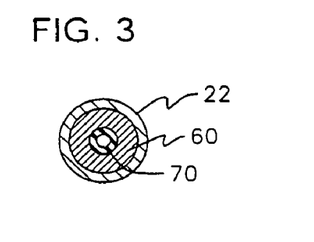
FIG. 3 is a section taken along line 3-3 of the surgical apparatus for use in fascial cleft surgery forming the present invention.

Next, the surgical apparatus includes an elastic dissection balloon 40. The dissection balloon is movably positioned within the applicator at the distal end thereof adjacent the introducing flange. The dissection balloon is reversibly expandable between a deflated condition and an expanded condition. Further, the dissection balloon is movable from a first storage position within the hollow tube body of the applicator to a second position exterior thereof as shown in FIGS. 1 and 2. Once the balloon is exterior the applicator it may be inflated and subsequently deflated. The dissection balloon is formed of a chosen elastic material having a tensile less than the tensile strength of the points of fusion between two layers of fascia such that the dissection balloon fails prior to achieving pressures that would destroy the anatomic boundaries of the fascial cleft such that a working space is demonstrated not created. See FIG. 8. The dissection balloon is formed of a thin walled elastic member with no inherent predetermined inflated shape. The balloon easily expands in all directions when not contained by a delimiting vessel or the like. When positioned within a fascial cleft, expansion of the balloon is shaped by the inherent dimensions of the anatomy of the fascial cleft. Accordingly, the dissection balloon is formed of a material capable of generating a force greater than the resistance of the loose areaolar tissue 16 between the two layers of fascia but lesser than the force generated by the integrity of the layers of fascia themselves or the anatomic fusion points of those layers.

Additionally, the surgical apparatus includes a gripping handle 50. the gripping handle is coupled to the applicator at the open proximal end 26 thereof. The gripping handle includes a thumb engaging recess 52 which corresponds to the introducing flange for allowing a user to judge the orientation of the introducing flange during use of the apparatus.

Further, a hollow introducing rod 60 is provided. The introducing rod is slideably positioned within the applicator 20. The rod includes a first end 62 terminating in a concave surface 64 positioned adjacent the dissection balloon for positioning the dissection balloon exterior the applicator to within an anatomic space for subsequent inflation and deflation. The introducing rod also has a second end 66 extending exterior the proximal end of the applicator. In use, the applicator's hollow tube body member 22 may be slide completely away from the introducer rod.

Finally, the preferred embodiment of the present invention includes a fill tube 70. The fill tube extends through the hollow introducing rod to the dissection balloon and is operably associated with the dissection balloon for inflating and deflating.

Figure 4:
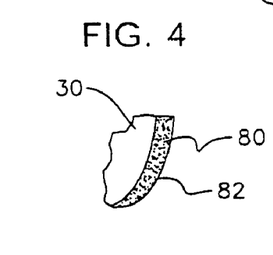
FIG. 4 is an enlarged view of the introducing flange as indicated by the numeral 4 in FIG. 1 of the present invention.
Figures 5, 6:
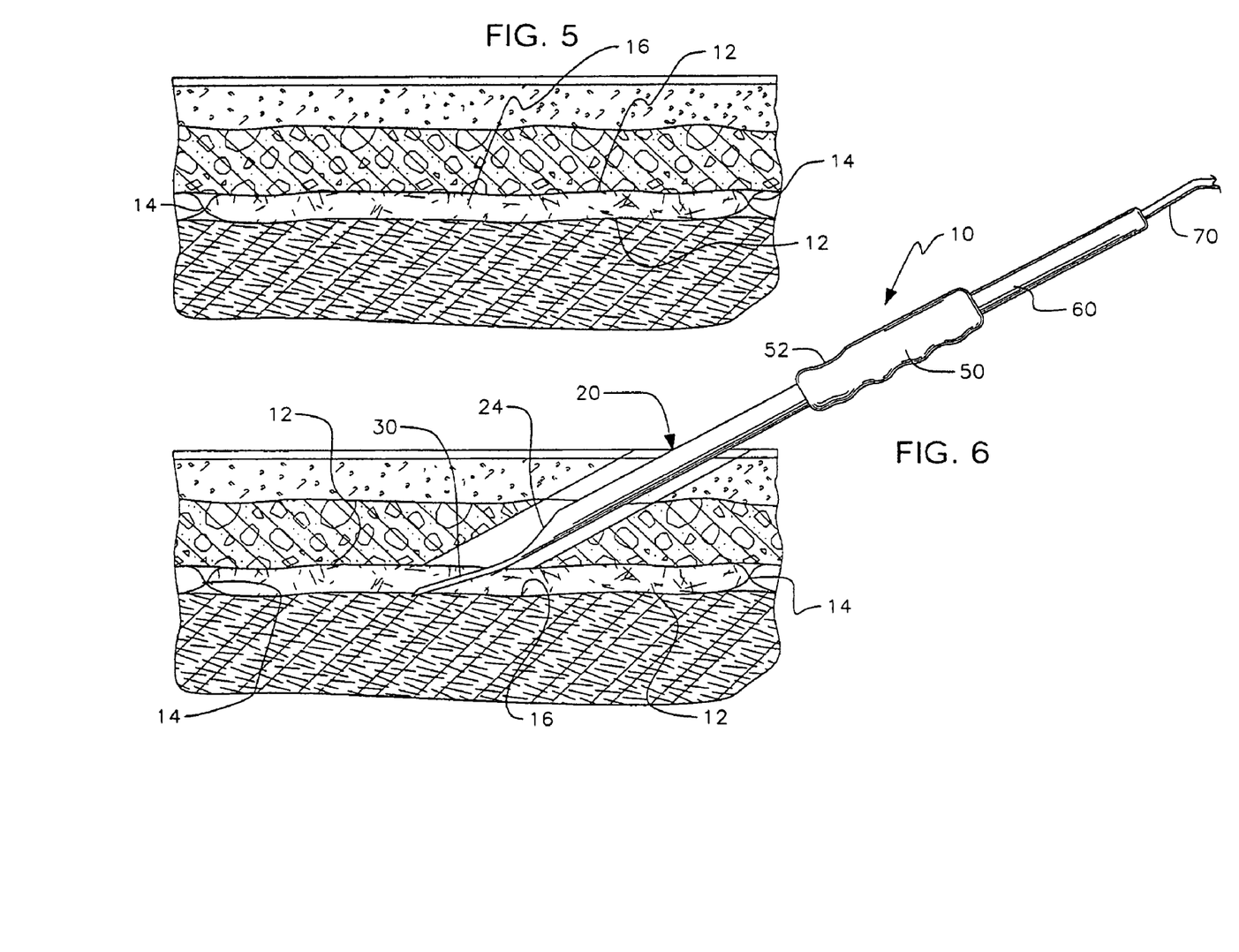
FIG. 5 is a cross-sectional view of anatomical tissue forming a fascial cleft.
FIG. 6 shows the surgical apparatus for use in fascial cleft surgery in use being inserted into an incision.
Figure 7:
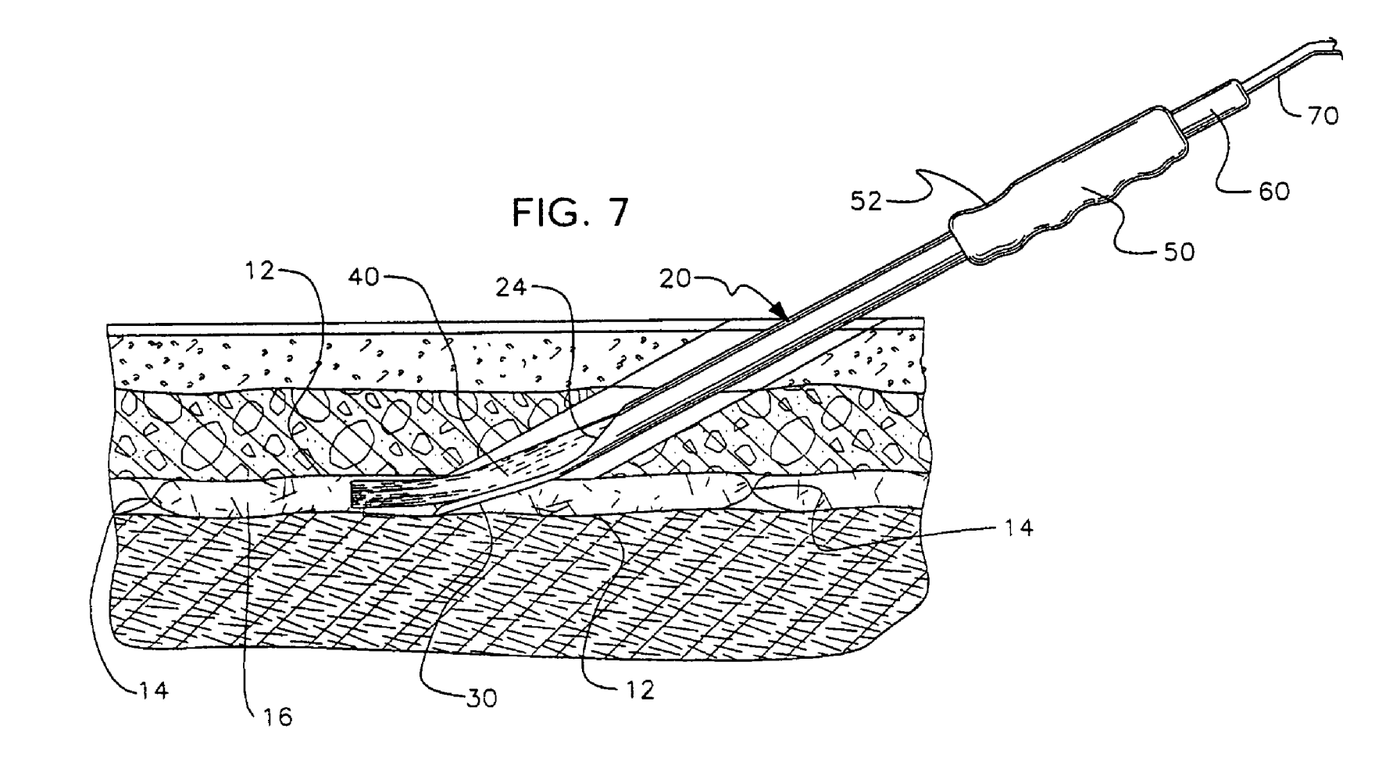
FIG. 7 shows the surgical apparatus for use in fascial cleft surgery being introduced into a fascial cleft and the dissection bag being introduced therein.
Figure 8:
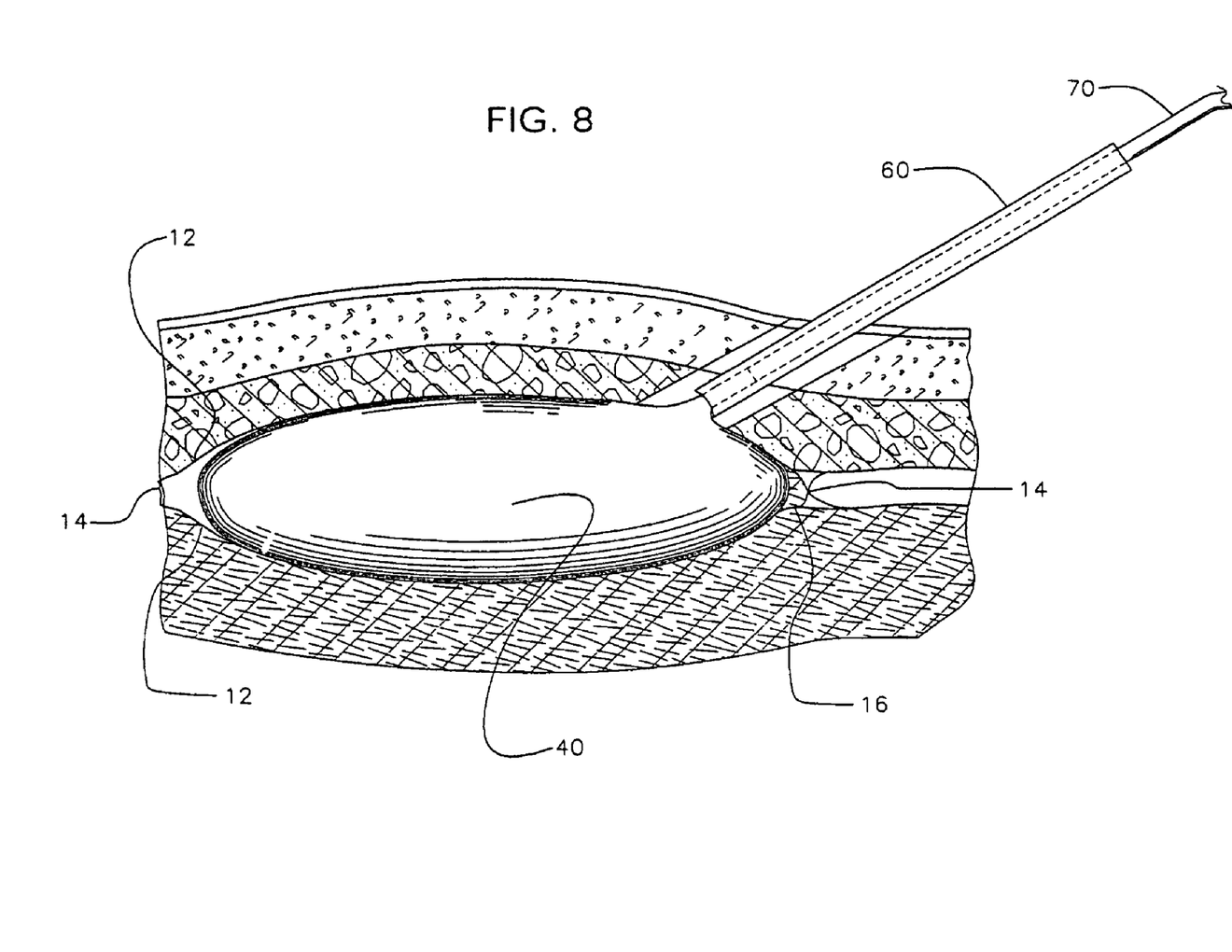
FIG. 8 shows the inflation of the dissection balloon within a fascial cleft.

As an alternate embodiment of the present invention, the malleable introducing flange may include a luminescent material 80 disposed about the peripheral edge 82 thereof for providing work area illumination. See FIG. 4.

In use, once the flange has guided the applicator to within a fascial cleft, the introducer rod is utilized to deploy the dissection balloon to within a fascial cleft. The applicator is slidably removed from introducer rod and the fascial cleft leaving the inflatable dissection balloon within in the cleft. The fill tube is used to inflate the dissection balloon with air, gas, or other suitable solution such as saline, until the limits of the fascial cleft have been reached and demonstrated. The introducing rod remains such that its concave face is within the fascial cleft is whereby its first end is in the open incision to prevent the inflatable device from extruding from within the access incision. See FIG. 8. Finally the device is deflated and removed.

As to the manner of usage and operation of the present invention, one such preferred method of use, endoscopically assisted components separation technique for ventral hernia repair, may be described. Assuming the apparatus has been assembled as in FIG. 10, the procedure is begun with the human patient placed in the supine position, with the entire abdomen prepped and draped in sterile fashion. The patient having been placed under a general anesthesia, an incision is made (approximately two to three centimeters long) over the lower to mid, lateral abdominal wall. This incision is aligned with the para median line along the nipple or mid clavicular position. The incision is made through the skin and subcutaneous fat and deepened through two layers of superficial fascia until the deep fascia of the external oblique muscle is exposed. This is incised under direct vision one centimeter lateral to the anatomic landmark known as the semi lunar line (lateral border of the rectus abdominis muscle). The open distal end of the device is next inserted into the fascial cleft between the external oblique and internal oblique which has been exposed by the described open dissection. The introducing flange's malleable spoonbill shaped end allows for placement into the fascial cleft without inadvertently straying from the desired anatomic space. Once inserted into the cleft, the introducing rod of the device is used to deliver the elastic dissection balloon into the fascial cleft. The applicator is then removed from the cleft and the elastic balloon member is held in position with the introducing rod to prevent it from backing out of the wound as expansion of the balloon is begun. The elastic balloon is inflated with saline or air. The shape of the dissection balloon is determined solely by the dimensions of the anatomic cleft. The balloon is inflated until it reaches the ligaments or anatomic boundaries of the inter-oblique muscle cleft. This is comprised of the semi lunar line medially, inguinal canal inferiorly, seventh costal interspace superiorly, and the para spinous line posteriorly. Once expansion to these boundaries is observed, additional inflation of fluid or air will not dissect past these stated boundaries. The contra lateral side is the operated upon in the same fashion. With the fascial cleft dissection complete the dissection balloons can be left in the inflated position for a period of immediate tissue expansion. This helps to undo the contraction of the lateral abdominal wall that takes place in ventral hernia formation. Attention is then turned to the abdominal midline defect. It can be approached through a laparoscopic or open surgical technique depending on the condition of the overlying tissues and other patient and hernia related considerations. In instances where poor quality skin and soft tissue coverage exists, it is excised at this time in an elliptical fashion, as part of the exposure of the underlying hernia sac. Depending on whether there has been a history of incarceration of intestines in the hernia, the sac may require opening and resection followed by lysis of intestinal adhesions. Now that preparations are complete for repair of the midline linea alba, the balloon dissectors are deflated and removed. Endoscopic telescopes are then inserted into the oblique muscle fascial clefts and laparoscopic cautery spatulas are used to divide the external oblique fascia one centimeter lateral to the semi lunar line. The length of the fascial relaxing incision depends on the size of the hernia defect and therefore the need for rectus mobilization. In very large hernias the fascial release extends from above the costal margin to the inguinal canal below. Now with the fascial cleft balloon dissection of the external oblique from the internal oblique, and associated immediate tissue expansion, the endoscopic release of the external oblique fascia allows for mobilization of the rectus muscles to the midline without undue tension. The closure of the midline rectus fascia with a running permanent suture is accomplished at this time. Wound closure is performed to complete the procedure.

Endoscopic components separation technique for ventral hernia repair makes use of the present invention to perform fascial cleft surgery in a quick, easy, accurate and complete fashion through a minimal incision. It also allows for immediate tissue expansion to lesson tension on the midline closure. Use of the device for minimally invasive skin sparing mastectomy exemplifies another use of the device—demonstration of the dimensions and size of a particular anatomic fascial cleft. The procedure is begun with a one centimeter incision on the lateral aspect of the inframammary fold crease. Open dissection is performed to the retro mammary fascial cleft. The device is inserted making use of the spoonbill distal end to insert the applicator into the cleft. Once the introducer has delivered the elastic balloon into the retro mammary space, the balloon is inflated until expansion is observed to have stopped at the anatomic boundaries of the circum mammary ligament. The balloon is then deflated and the mastectomy is begun with a circum areaolar incision. The overlying skin is dissected away from the breast tissue in an ongoing circular fashion. The open dissection continues until the attachment of the skin to the chest wall is approached. This is the critical point in the procedure as every bit of the breast gland must be removed without overshooting the circum mammary ligament. Next the balloon which has already performed a dissection under the breast to the boundaries of the circum mammary ligament is partially inflated. This allows connection of the two dissection planes (retro mammary cleft and subcutaneous mastectomy plane) at the para sternal location through open dissection. The balloon is then deflated and removed before the connecting of the two planes of dissection is completed by open dissection in circular fashion; starting first in the direction of the inframammary fold, followed by dissection towards the superior aspect of the breast, saving the lateral aspect for last. The lateral boundary of the breast's attachment to the chest is the most critical and yet most indistinct. It is in this region that the device's dissection footprint is therefore most helpful. Since all other attachments of the breast to the skin and chest wall have been divided the breast can be delivered out through the circum areaolar incision. The surgeon then identifies the last remaining tissue that requires division through bi-manual palpation of the tissue bridge between the sub cutaneous dissection and device created sub glandular dissection. This tissue is carefully divided and the mastectomy is complete. An en-block axillary node dissection is carried out through the circum areaolar incision to complete the modified radical mastectomy. Breast reconstruction follows directly, using a TRAM flap or implant covered by a Latissimus Dorsi flap.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the alt, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method of repairing a ventral hernia, comprising the steps of:
   first inserting a distal end of a tubular applicator into a fascial cleft between external oblique and internal oblique muscles, the applicator terminating in a distally extending malleable flange that is reconfigurable from a first configuration to a second configuration upon application of a force, wherein the introducing flange remains in the second configuration when the force is removed;
   subsequent to inserting the tubular applicator, advancing a hollow rod within the tubular applicator into the fascial cleft to move an elastic balloon from within the tubular applicator to a position exterior thereof, the balloon moving over the flange so as to guide the balloon into the fascial cleft;
   wherein the balloon has a fill tube and the fill tube extends through the hollow rod so that the balloon is adjacent a distal end of the rod;
   after advancing the hollow rod, removing the tubular applicator and inflating the balloon through the fill tube so that a space is demonstrated between two layers of anatomically defined fascia, a shape of the inflated balloon being determined by the dimensions of the fascial cleft; and
   repairing the hernia defect.

2. The method of claim 1, wherein the rod has a concave distal end positioned adjacent the balloon.

3. The method of claim 1, wherein the rod extends into the fascial cleft for preventing the balloon from expanding in a proximal direction.

4. The method of claim 1, wherein the balloon is inflated so as to expand the tissue of the abdominal wall.

5. The method of claim 1, wherein the shape of the fully inflated balloon conforms to the inherent dimensions of an anatomy of the fascial cleft.

* * * * *